United States Patent
Hayami et al.

(10) Patent No.: US 12,361,685 B2
(45) Date of Patent: Jul. 15, 2025

(54) TRAINING DATA GENERATING SYSTEM, METHOD FOR GENERATING TRAINING DATA, AND RECORDING MEDIUM

(71) Applicant: OLYMPUS CORPORATION, Tokyo (JP)

(72) Inventors: Takehito Hayami, Yokohama (JP); Makoto Kitamura, Hachioji (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 380 days.

(21) Appl. No.: 17/939,136

(22) Filed: Sep. 7, 2022

(65) Prior Publication Data
US 2023/0005245 A1   Jan. 5, 2023

Related U.S. Application Data

(63) Continuation of application No. PCT/JP2020/009909, filed on Mar. 9, 2020.

(51) Int. Cl.
*G06T 7/00* (2017.01)
*G06V 10/772* (2022.01)
*G06V 10/774* (2022.01)

(52) U.S. Cl.
CPC .......... *G06V 10/774* (2022.01); *G06T 7/0012* (2013.01); *G06V 10/772* (2022.01)

(58) Field of Classification Search
CPC .............. G06V 10/774; G06V 10/772; G06V 2201/03; G06T 7/0012; G06T 11/00; A61B 1/045; A61B 5/00

(Continued)

(56) References Cited

U.S. PATENT DOCUMENTS

2009/0309961 A1   12/2009   Miyashita
2010/0165088 A1*   7/2010   Seo ............ A61B 1/0005
                                                 348/E7.085

(Continued)

FOREIGN PATENT DOCUMENTS

JP   2009-297365 A   12/2009
JP   2013-254286 A   12/2013

(Continued)

OTHER PUBLICATIONS

International Search Report dated Jun. 2, 2020 received in PCT/JP2020/009909.

*Primary Examiner* — Huy C Ho
(74) *Attorney, Agent, or Firm* — Scully, Scott, Murphy & Presser, P.C.

(57) ABSTRACT

A training data generating system includes a processor. The processor acquires a plurality of medical images. The processor associates medical images with each other which are included in the plurality of medical images based on similarities of an imaging target to generate an associated image group including medical images associated with each other. The processor outputs, to a display, an application target image to be an image as an application target of representative training information based on the associated image group. The processor accepts input of representative contour information indicative of a contour of a specific region in the application target image as the representative training information. The processor applies contour information, as training information, to each medical image included in the associated image group based on the representative training information input to the application target image.

20 Claims, 18 Drawing Sheets

(58) Field of Classification Search
USPC .......................................................... 382/159
See application file for complete search history.

(56) References Cited

U.S. PATENT DOCUMENTS

| | | | |
|---|---|---|---|
| 2017/0262598 A1* | 9/2017 | Petkov | .................. G06N 3/045 |
| 2019/0138852 A1 | 5/2019 | Lio et al. | |
| 2019/0313883 A1 | 10/2019 | Hosoya et al. | |

FOREIGN PATENT DOCUMENTS

| | | |
|---|---|---|
| JP | 2019-087012 A | 6/2019 |
| JP | 2019-118694 A | 7/2019 |
| WO | 2018/142664 A1 | 8/2018 |

\* cited by examiner

FIG. 4

|     | IX1 | IX2 | IX3 | IX4 | IX5 |
|-----|-----|-----|-----|-----|-----|
| IX1 |     | ○   | ○   | ×   | ×   |
| IX2 | ○   |     | ○   | ×   | ○   |
| IX3 | ○   | ○   |     | ○   | ×   |
| IX4 | ×   | ×   | ○   |     | ○   |
| IX5 | ×   | ○   | ×   | ○   |     |

FIG. 11
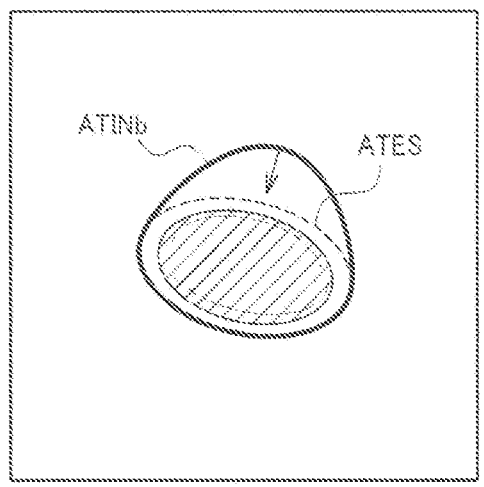
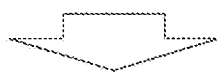
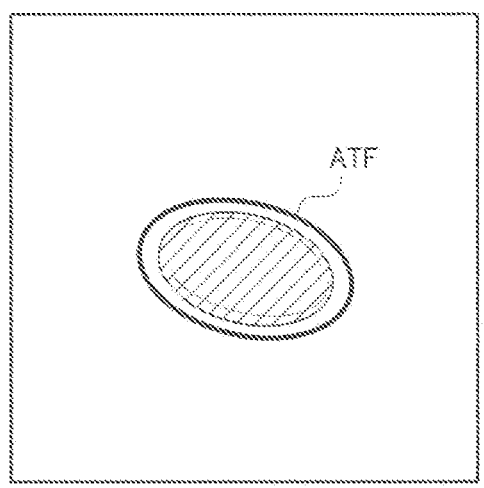

TRAINING DATA GENERATING SYSTEM, METHOD FOR GENERATING TRAINING DATA, AND RECORDING MEDIUM

CROSS REFERENCE TO RELATED APPLICATION

This application is a continuation of International Patent Application No. PCT/JP2020/009909, having an international filing date of Mar. 9, 2020, which designated the United States, the entirety of which is incorporated herein by reference.

BACKGROUND

Machine learning, such as deep learning, has been widely used as an image recognition technique. The machine learning requires the input of a large number of training images suitable for learning. One of the methods to prepare such a large number of training images is data augmentation. The data augmentation is a method to increase the number of training images by processing the original images that are actually captured to generate new images. From the perspective of improving the recognition accuracy of machine learning, however, it is desirable to prepare a large number of original images to apply a teacher label to each of those original images. Japanese Unexamined Patent Application Publication No. 2019-118694 discloses a medical image generating device that generates images for machine learning of ultrasonic diagnostic equipment. Also in Japanese Unexamined Patent Application Publication No. 2019-118694, the medical image generating device sets, as an image of interest, a medical image displayed when the user performed an image save or freeze operation, and mechanically extracts a plurality of images similar to such image of interest from time series images. The user applies label information to the image of interest. The medical image generating device applies the label information to the plurality of images similar to the image of interest based on the label information attached to the image of interest.

SUMMARY

In accordance with one of some aspect, there is provided a training data generating system comprising a processor, the processor being configured to implement:
  acquiring a plurality of medical images;
  associating medical images with each other which are included in the plurality of medical images based on similarities of an imaging target to generate an associated image group comprising medical images associated with each other;
  outputting, to a display, an application target image to be an image as an application target of representative training information based on the associated image group;
  accepting input of representative contour information indicative of a contour of a specific region in the application target image as the representative training information; and
  applying contour information, as training information, to each medical image included in the associated image group based on the representative training information input to the application target image.

In accordance with one of some aspect, there is provided a method of generating training data, the method comprising:
  acquiring a plurality of medical images;
  associating medical images with each other which are included in the plurality of medical images based on similarities of an imaging target to generate an associated image group comprising medical images associated with each other;
  outputting, to a display, an application target image to be an image as an application target of representative training information based on the associated image group;
  accepting input of representative contour information indicative of a contour of a specific region in the application target image as the representative training information; and
  applying contour information, as training information, to each medical image included in the associated image group based on the representative training information input to the application target image.

In accordance with one of some aspect, there is provided a non-transitory computer readable recording medium storing thereon a computer program that causes a computer to perform a method comprising:
  acquiring a plurality of medical images;
  associating medical images with each other which are included in the plurality of medical images based on similarities of an imaging target to generate an associated image group comprising medical images associated with each other;
  outputting, to a display, an application target image to be an image as an application target of representative training information based on the associated image group;
  accepting input of representative contour information indicative of a contour of a specific region in the application target image as the representative training information; and
  applying contour information, as training information, to each medical image included in the associated image group based on the representative training information input to the application target image.

BRIEF DESCRIPTION OF THE DRAWINGS

FIG. 4 illustrates a method of determining an associated image group.

FIG. 11 illustrates a first operation example of an input adjuster.

DESCRIPTION OF EXEMPLARY EMBODIMENTS

Figure 1:
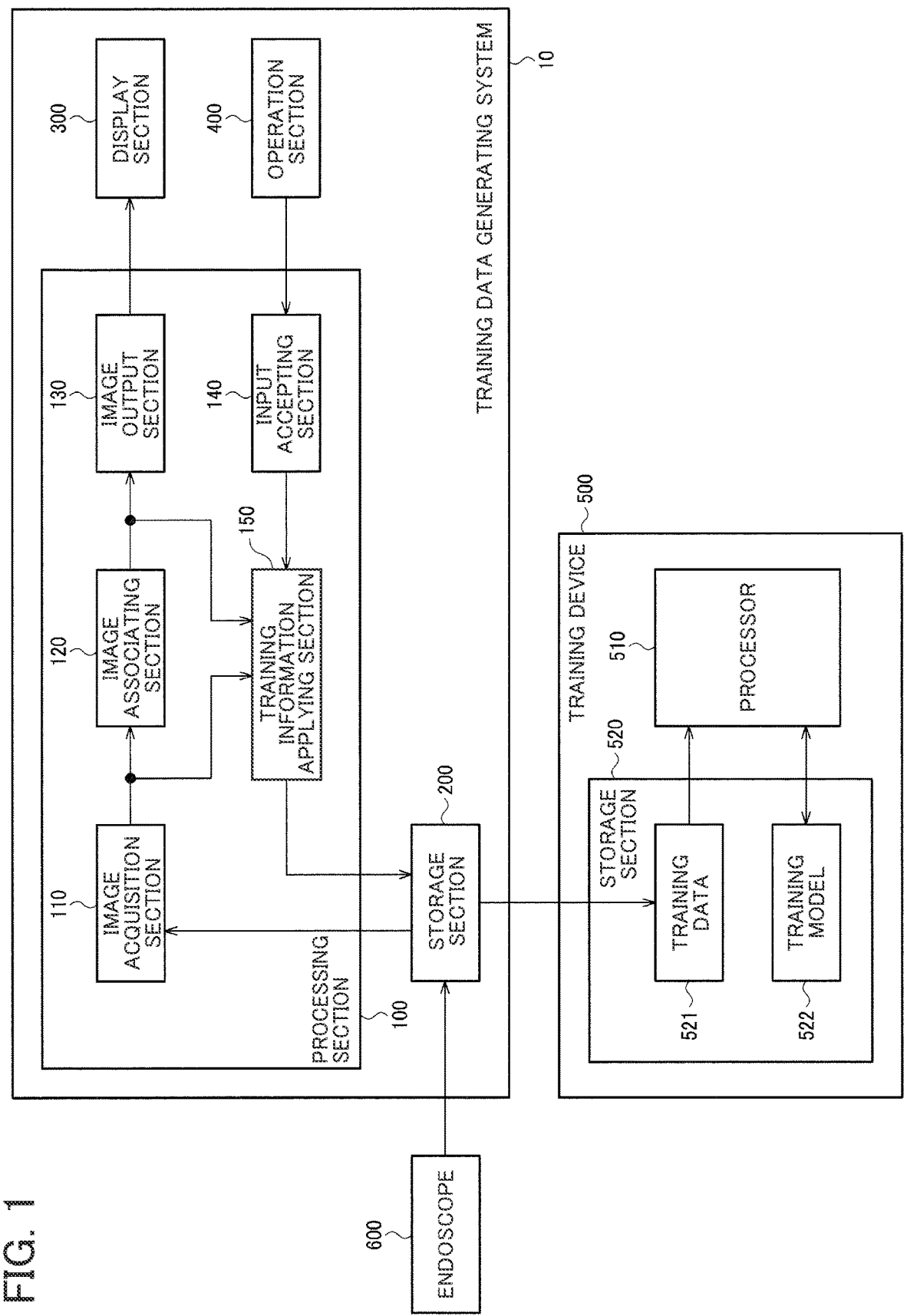
FIG. 1 illustrates a first configuration example of a training data generating system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. First Configuration Example

In Japanese Unexamined Patent Application Publication No. 2019-118694 described above, the image obtained when the user performs an image save or freeze operation becomes an image of interest. This results in that an image with low similarity to time series images or with a small number of images with high similarity among the time series images may be the image of interest. In this case, the problem exists that, with label information applied to the image of interest, a medical image generating device fails to apply the label information to the time series images or applies the label information to only a small number of images. For example, in a case where an image captured when the angle of camera in such as an endoscope is temporarily changed significantly becomes the image of interest, the label information may not be applied, based on the similarity, to the images captured at angles other than that angle.

FIG. 1 illustrates a first configuration example of a training data generating system 10. The training data generating system 10 includes a processing section 100, a storage section 200, a display section 300, and an operation section 400. Note that when the training data generating system 10 generates training data, an endoscope 600 and a training device 500, which are illustrated in FIG. 1, do not need to be connected to the training data generating system 10.

The processing section 100 includes an image acquisition section 110, an image associating section 120, an image output section 130, an input accepting section 140, and the training information applying section 150. The image acquisition section 110 acquires a plurality of medical images. The image associating section 120 associates medical images with each other which are included in the plurality of medical images based on similarities of an imaging target to generate an associated image group. The associated image group represents a group including medical images associated with each other at the above-described association. The image output section 130 outputs, to the display section 300, an application target image to be an image as an application target of representative training information based on the associated image group. The input accepting section 140 accepts input of the representative training information from the operation section 400. The training information applying section 150 applies training information to the medical images included in the associated image group based on the representative training information input for the application target image.

With such a configuration, the application target image, which is displayed on the display section 300 in order for the user to apply the training information, is displayed based on the associated image group to which the association has been made on the basis of the similarity of the imaging target. That is, since the similarity is determined prior to presentation to the user, the application target image is an image that has similarity to each medical image of the associated image group. This allows the representative training information to be attached to the medical images associated with a large number of images with high similarity, so that the training information applying section 150 can automatically apply the training information to a larger number of medical images based on a single piece of representative training information. Consequently, this can reduce the number of application target images that require the user to input the representative training information, allowing the user to generate a training image with fewer work steps.

Details of the training data generating system 10 illustrated in FIG. 1 will be described below.

The training data generating system 10 is an information processing device such as a personal computer (PC). Alternatively, the training data generating system 10 may be a system in which a terminal device and the information processing device are connected through a network. For example, the terminal device includes the display section 300, the operation section 400, and the storage section 200, and the information processing device includes the processing section 100. Still alternatively, the training data generating system 10 may be a cloud system in which a plurality of information processing devices is connected to each other through a network.

The storage section 200 stores a plurality of medical images captured with the endoscope 600. The medical images are in vivo images captured with a medical endoscope. The medical endoscope is a videoscope including a gastrointestinal endoscope, or a surgical rigid scope, for example. The medical images are the time series images. For example, the endoscope 600 captures a video of the interior of the body, and the image of each frame in the video corresponds to each of the medical images. The storage section 200 is a storage device such as a semiconductor memory and a hard disk drive. The semiconductor memory is, for example, a volatile memory such as a random-access memory (RAM) or a non-volatile memory such as an electrically erasable programmable read only memory (EE-PROM).

The processing section 100 is a processor. The processor may be an integrated circuit device such as a central processing unit (CPU), a microcomputer, a digital signal processor (DSP), an application-specific integrated circuit (ASIC) or a field-programmable gate array (FPGA). The processing section 100 may include one or more processors. The processing section 100 as the processor may be, for example, a processing circuit or a processing device each including one or more circuit elements, or a circuit device in which one or more circuit elements are mounted on the board.

Figure 8:
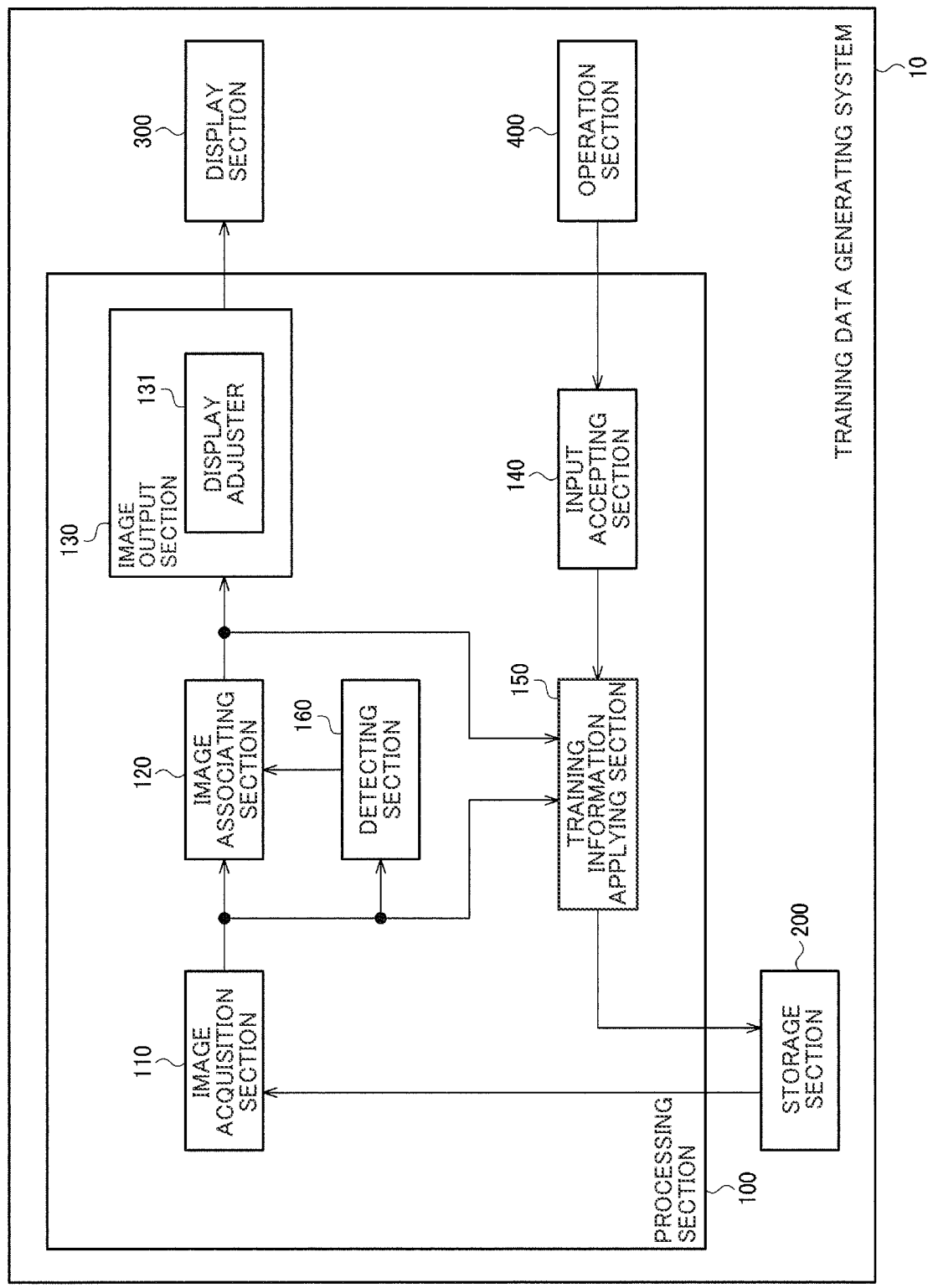
FIG. 8 illustrates a configuration example of the training data generating system in a third modification of the first configuration example.

An operation of the processing section 100 may be implemented by software processing. That is, the storage section 200 stores a program in which operations of all or a part of the image acquisition section 110, the image associating section 120, the image output section 130, the input accepting section 140, and the training information applying section 150 each included in the processing section 100 are described. The processor executes the program stored in the storage section 200, so that the operations of the processing section 100 are implemented. Note that the program may be one in which a detecting section 160 mentioned below in FIG. 8 is further described. The above-mentioned program may be stored in an information storage medium, which is a computer readable storage medium. The information storage medium can be implemented by, for example, an optical disk, a memory card, a hard disk drive (HDD), or a semiconductor memory. The computer is a device provided with an input device, a processing section, a storage section, and an output section.

Figure 2:
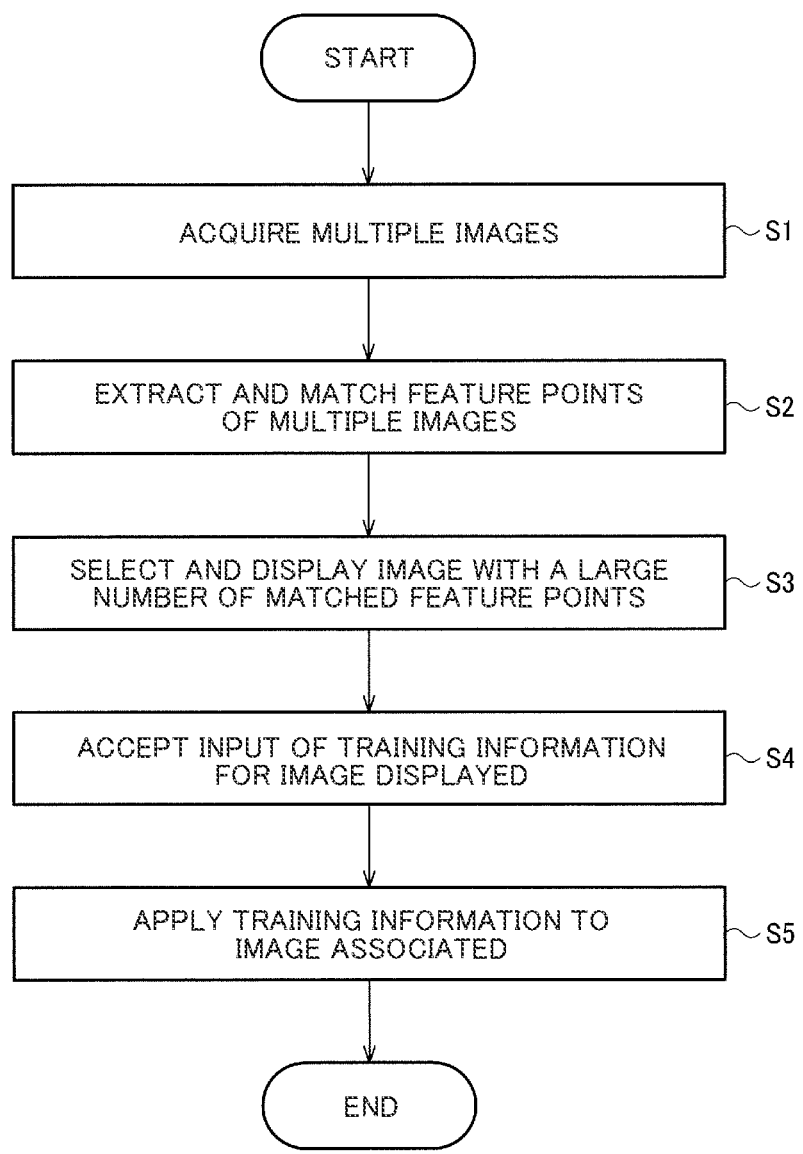
FIG. 2 is a flowchart illustrating a flow of process in the first configuration example.

FIG. 2 is a flowchart illustrating a flow of process in the first configuration example. In step S1, the image acquisition section 110 acquires a plurality of medical images. Specifically, the image acquisition section 110, which is an access control section that reads data from the storage section 200, acquires the plurality of medical images from the storage section 200 to output the plurality of medical images to the image associating section 120.

In step S2, the image associating section 120 extracts feature points of the plurality of medical images to perform matching between the images for each feature point. In step S3, the image associating section 120 selects the medical image with a large number of matched feature points. The image output section 130 outputs, to the display section 300, the selected medical image as an application target image. The display section 300 displays the application target image. The display section 300 is a display such as a liquid crystal display device or an electro luminescence (EL) display device.

In step S4, the input accepting section 140 accepts input of training information for the displayed application target image. That is, the user uses the operation section 400 to apply the training information to the application target image displayed on the display section 300. The applied training information is input to the input accepting section 140. The input accepting section 140 is a communication interface between, for example, the operation section 400 and the processing section 100. The operation section 400 is a device for the user to perform operation input or information input to the training data generating system 10, such as a pointing device, a keyboard, or a touch panel.

In step S5, the training information applying section 150 applies, based on the applied training information to the application target image, the training information to each medical image associated by the image associating section 120 to store the training information in the storage section 200. The medical image to which training information is applied is hereinafter referred to as a training image.

The training image stored in the storage section 200 is input to the training device 500. The training device 500 includes a storage section 520 and a processor 510. The training image input from the storage section 200 is stored as training data 521 in the storage section 520. The storage section 520 stores a training model 522 of machine learning. The processor 510 uses the training data 521 to perform machine learning on the training model 522. The machine-learned training model 522 is transferred to an endoscope as a trained model to be used for image recognition in the endoscope.

Figure 3:
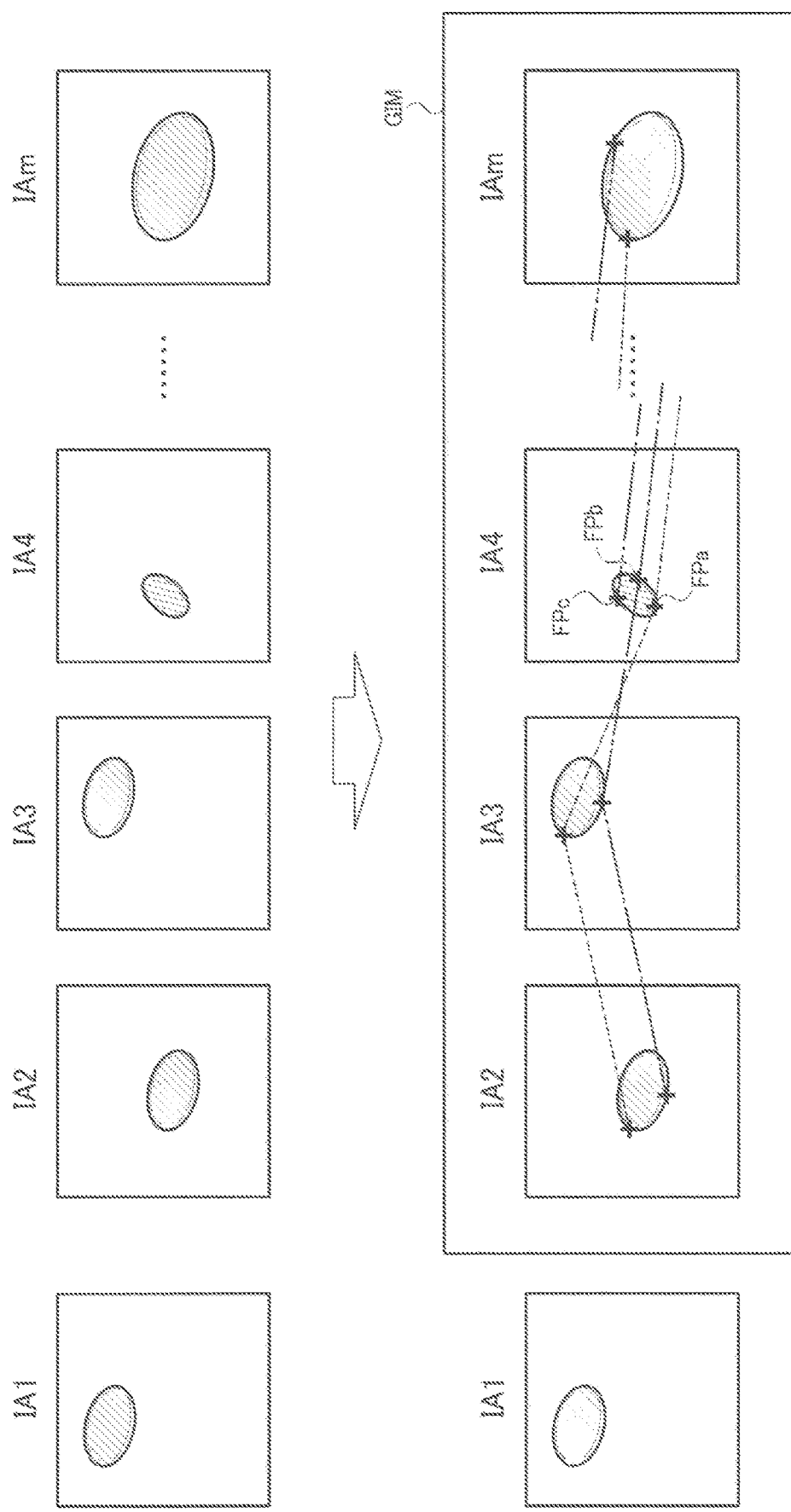
FIG. 3 illustrates an operation of an image associating section.

FIG. 3 illustrates an operation of the image associating section 120. In FIG. 3, IA1 to IAm denote a plurality of medical images obtained by the image acquisition section 110 where m is an integer equal to or greater than three. Here, it is defined as m=5, more specifically, IAm=IA5.

In FIG. 3, no feature point is detected in IA1, the common feature points FPa are detected in IA2 to IA5, the common feature points FPb are detected in IA2 to IA4, and the common feature points FPc are detected in IA4 and IA5. The feature point indicates a feature of an image and is a point characterized by a feature amount detected in the image. Various feature amounts can be assumed, which include, for example, edges or gradients in an image or their statistics. The image associating section 120 extracts the feature point with methods such as the Scale Invariant Feature Transform (SIFT), the Speeded-Up Robust Features (SURF), and the Histograms of Oriented Gradients (HOG).

The image associating section 120 determines a group of images with high similarity among imaging targets as an associated image group GIM based on the feature points FPa to FPc. The "similarities of an imaging target" refers to the degree to which target objects seen in the medical images are similar where the higher the similarity, the more likely the target objects are identical. It can be determined that when employing the feature points, the greater the number of feature points in common, the higher the similarity of imaging targets to each other. The image associating section 120, for example, associates medical images in which the number of the feature points in common is equal to or more than a threshold. In the example of FIG. 3, the image associating section 120 associates the medical images that each have two or more feature points in common. The image associating section 120 determines IA2 to IA4 and IAm as the associated image group GIM since IA4 has two or more feature points in common with each of IA2, IA3, and IAm.

Figure 4:
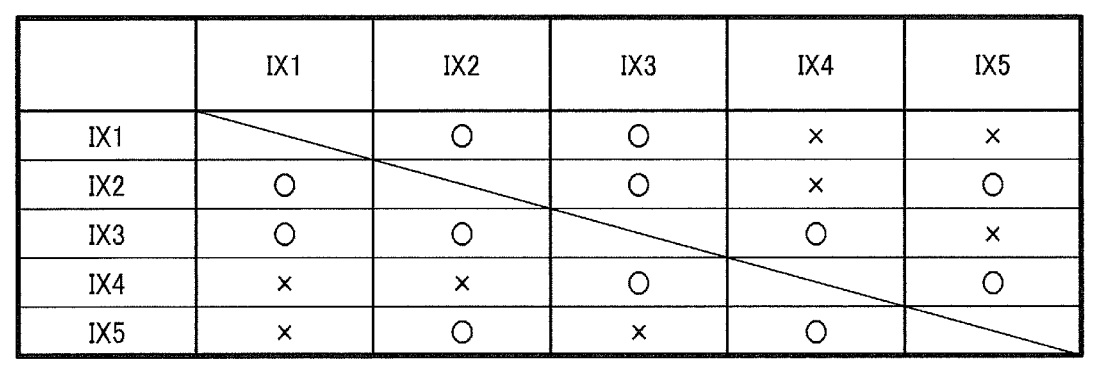

FIG. 4 illustrates a method of determining the associated image group. Here, IX1 to IX5 are assumed to be obtained as a plurality of medical images. The image associating section 120 determines the similarity between each of the medical images IX1 to IX5 and the other medical image. A circle mark indicates that a high similarity is determined while a cross mark indicates that a low similarity is determined. IX1, IX2, IX3, IX4, and IX5 are determined to be highly similar to two, three, three, two, and two of medical images, respectively.

The image associating section 120 selects, as an application target image, the medical images that each have a large number of highly similar medical images and determines, as the associated image group, the medical images with high similarity to the application target image. In the example of FIG. 4, IX2 is selected as the application target image and IX1 to IX3 and IX5 are set as the associated image group.

Alternatively, IX3 is selected as the application target image and IX1 to IX4 are set as the associated image group. The image associating section 120 may select, for example, the image with the smaller number between IX2 and IX3 or equivalently the preceding image in the time series as the application target image. Still alternatively, the image associating section 120 may select those as one associated image group in consideration of another associated image group, such as determining IX1 to IX3 and IX5 as the associated image group when IX4 is included in the other associated image group.

Figure 5:
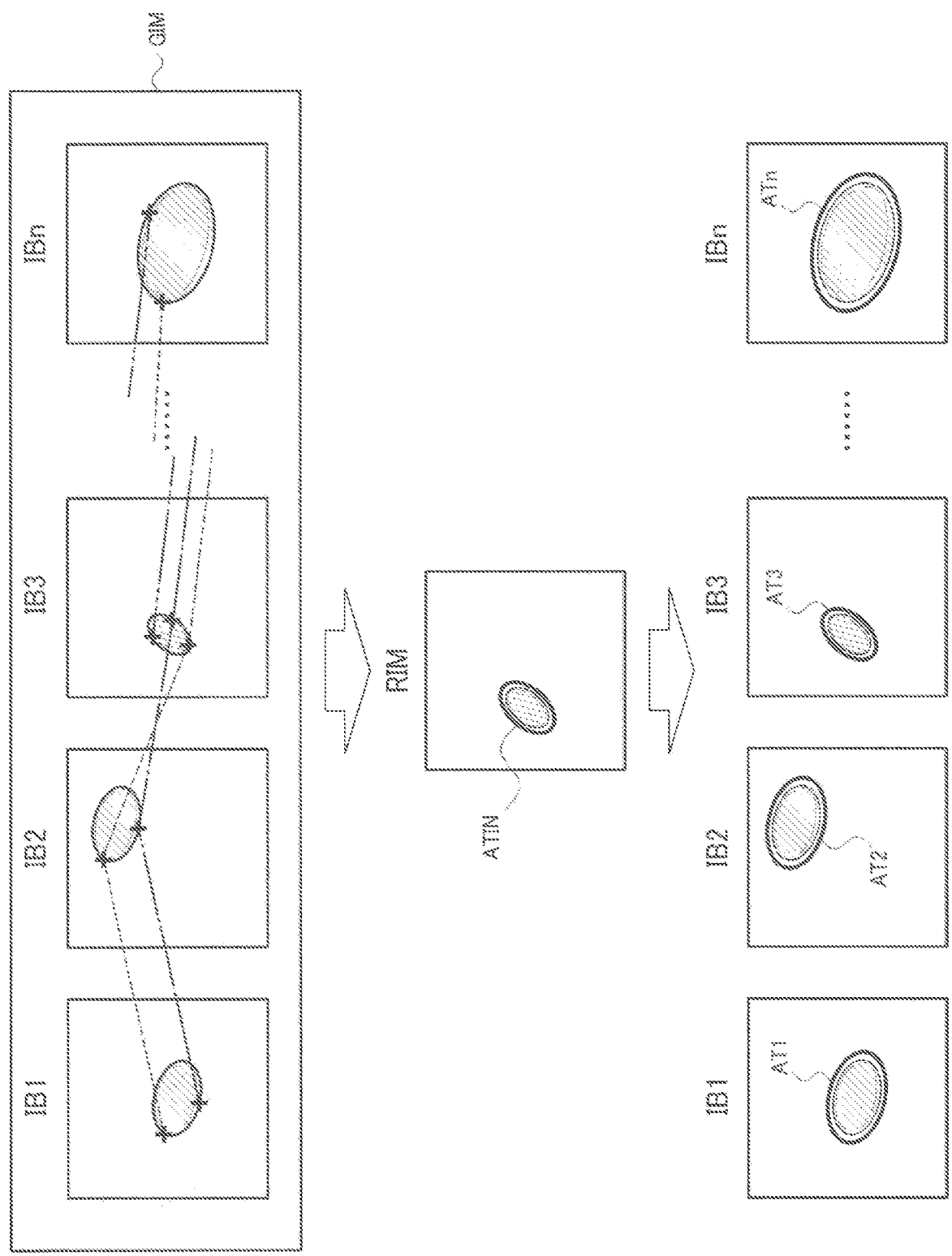
FIG. 5 illustrates operations of an image output section, an input accepting section, and a training information applying section.

FIG. 5 illustrates operations of the image output section 130, the input accepting section 140, and the training information applying section 150. In FIG. 5, reference designators IB1 to IBn correspond to IA2 to IAm in FIG. 3. With the method described in FIG. 4, the medical image IB3 among those IB1 to IBn, which belong to the associated image group GIM, is selected as an application target image RIM. The n is an integer equal to or greater than two.

The image output section 130 displays the application target image RIM selected by the image associating section 120 on the display section 300. The user applies a representative training information ATIN to the application target image RIM through the operation section 400. The representative training information ATIN refers to training information applied to the application target image RIM. FIG. 5 diagrammatically illustrates an example where the training information is contour information surrounding a detection target for machine learning. The training information may be a text, a bounding box, a contour, or a region. The text is the information used as artificial intelligence (AI) training data that performs a classification process. The text is the information that indicates the content or conditions of an imaging target, such as the type of lesion or the grade of the lesion. The bounding box is the information used as the AI training data that performs a detection process. The bounding box is a rectangle circumscribed on an imaging target such as a lesion and indicates the presence and position of the lesions. The contour or the region is the information used as the AI training data that performs a segmentation process. The contour is the information that indicates the boundary between the imaging target such as the lesion and the region other than the imaging target such as a normal mucosa. The region is the information that indicates the region occupied by the imaging target such as the lesion and contains information of the contour.

The training information applying section 150 applies training information AT1 to ATn to the respective medical images IB1 to IBn included in the associated image group GIM based on the representative training information ATIN accepted by the input accepting section 140. In FIG. 5, the representative training information ATIN as the training information AT3 is applied as it is to IB3 of the application target image RIM. The training information applying section 150 geometrically transforms the representative training information ATIN based on feature points to apply the training information to the medical images other than IB3. That is, in between two images that each have two or more feature points in common, parallel displacements, an amount of rotation, and a scaling factor between the images can be obtained on the basis of the positions and correspondence of and between such feature points. The training information applying section 150 converts the representative training information ATIN into the training information AT1, AT2, and AT4 to ATn by geometric transformation with the parallel displacements, the amount of rotation, and the scaling factor.

In accordance with the present embodiment, the image output section 130 outputs, to the display section 300, the medical images selected from the associated image group GIM as the application target image RIM.

With this processing, any of the medical images included in the associated image group GIM are displayed as the application target image RIM on the display section 300. Since the application target image RIM is associated with the other medical image in the associated image group GIM, such correlation can be used to apply the training information for each medical image based on the representative training information ATIN.

Additionally, in the present embodiment, the number of medical images associated with each medical image in the association based on similarities of an imaging target is considered as the number of associated images. For example, in FIG. 4, the number of associated images for IX1 to IX5 are two, three, three, two, and two, respectively. The image output section 130 outputs, to the display section 300, the medical images selected based on the number of associated images as the application target image RIM.

Specifically, the image associating section 120 selects the application target image RIM from the plurality of medical images based on the number of associated images to determine the medical images associated with the application target image RIM among the plurality of medical images as the associated image group GIM. More Specifically, the image associating section 120 selects the medical image with the highest number of associated images as the application target image RIM among the plurality of medical images in which the number of associated images is calculated.

This increases the number of images associated with a single application target image RIM, thus reducing the number of application target images RIM that require the user to attach the representative training information ATIN. This reduces the user's workload in generation of training images. Note that the image associating section 120 selects the application target image RIM in the above-described configuration example or alternatively, the image output section 130 may select the application target image RIM. For example, when there is a plurality of candidates with the same number of images with high similarity as in IX2 and IX3 of FIG. 4, the image output section 130 may select any of the plurality of candidates as the application target image. The image output section 130 may select such as those with a larger number of feature points included in each candidate image as the application target image.

Additionally, in the present embodiment, the input accepting section 140 accepts representative contour information indicative of a contour of a specific region in the application target image RIM as the representative training information ATIN. The training information applying section 150 applies the contour information to the medical images included in the associated image group GIM as the training information AT1 to ATn.

The specific region refers to a region that is targeted for detection by the AI being machine-learned based on the training images generated by the training data generating system 10. In accordance with the present embodiment, since the contour information indicative of the contour of the specific region is applied to the medical images as the respective training information AT1 to ATn, performing machine learning based on those training information enables detection of the specific region by segmentation.

Additionally, in the present embodiment, the image associating section 120 extracts the feature points FPa to FPc, each indicating a feature of an image, from each medical image in the plurality of medical images IA1 to IAm to perform the association of the medical images IB1 to IBn each including the feature point in common with each other out of the plurality of medical images IA1 to IAm, and thereby generates the associated image group GIM. The training information applying section 150 uses the common feature points FPa to FPc to apply the contour information indicative of the contour of the specific region to the medical images IB1 to IBn included in the associated image group GIM as the training information AT1 to ATn.

This enables application of the contour information to each medical image using information of the feature points that are matched when generating the associated image group GIM. As described above, in between the images that each have feature points in common, the representative contour information can be converted into the contour information of each medical image by geometric transformation.

2. Modifications of the First Configuration Example

Figure 6:
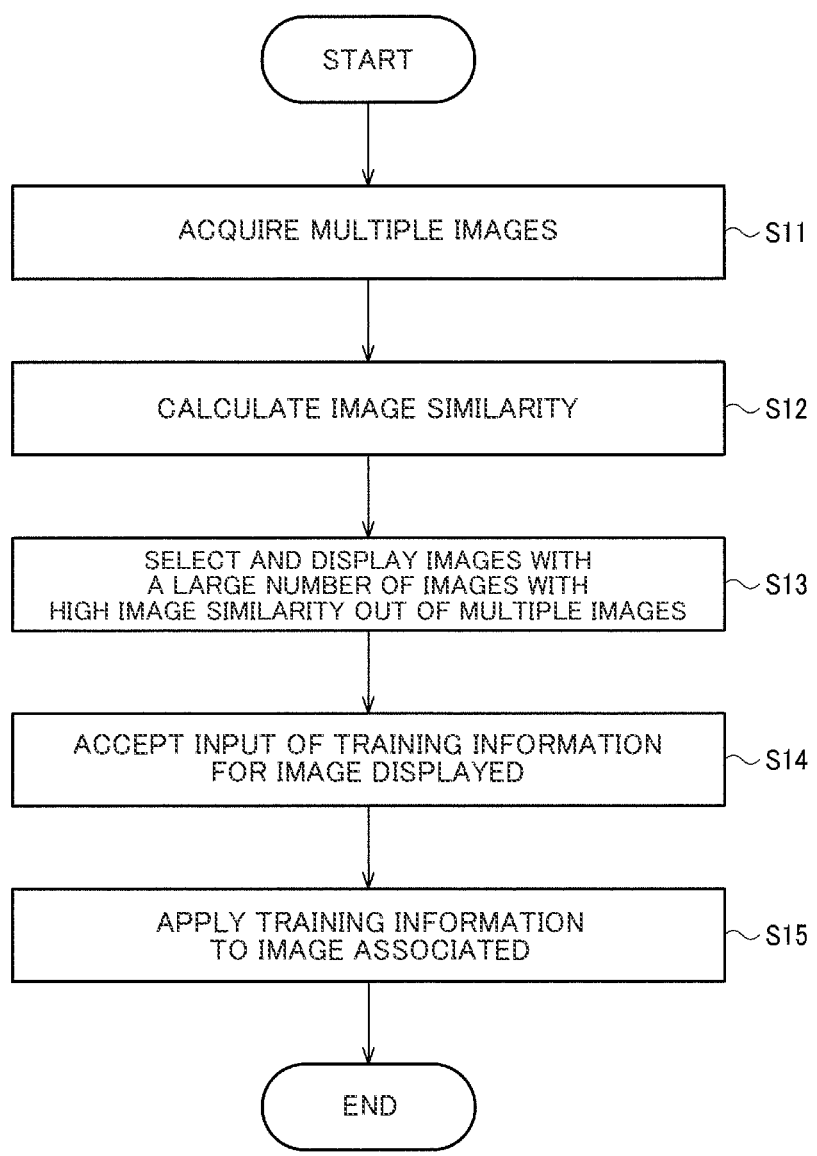
FIG. 6 is a flowchart illustrating a flow of process in a first modification of the first configuration example.

In a first modification, similarity of an imaging target is determined based on image similarity. A hardware configuration of the training data generating system 10 is the same as those in FIG. 1. FIG. 6 is a flowchart illustrating a flow of process in the first modification. A description of steps S11 and S15, which are similar to steps S1 and S5 in FIG. 2, respectively, is omitted here.

In step S12, the image associating section 120 calculates the image similarity between medical images included in a plurality of medical images. The image similarity is an index of how similar two images are, or equivalently, the index indicating a degree of the similarity of the images themselves. As long as images are similar to each other, the imaging targets seen in those images can be determined to be highly similar. The image similarity adopts, for example, the Sum of Squared Difference (SSD), the Sum of Absolute Difference (SAD), the Normalized Cross Correlation (NCC), and the Zero-mean Normalized Cross Correlation (ZNCC).

In step S13, the image associating section 120 selects images with a large number of images with high image similarity out of the plurality of medical images as application target images. The image associating section 120, for example, compares the image similarity and the threshold to determine the degree of the similarity. The methods of selecting the application target image and setting an associated image group are the same as those described in such as FIG. 4. The image output section 130 outputs the selected application target image to the display section 300.

In step S14, the input accepting section 140 accepts input of training information for the displayed application target image. Examples of the training information when employing the image similarity are considered to include, but are not limited to, a text.

Figure 7:
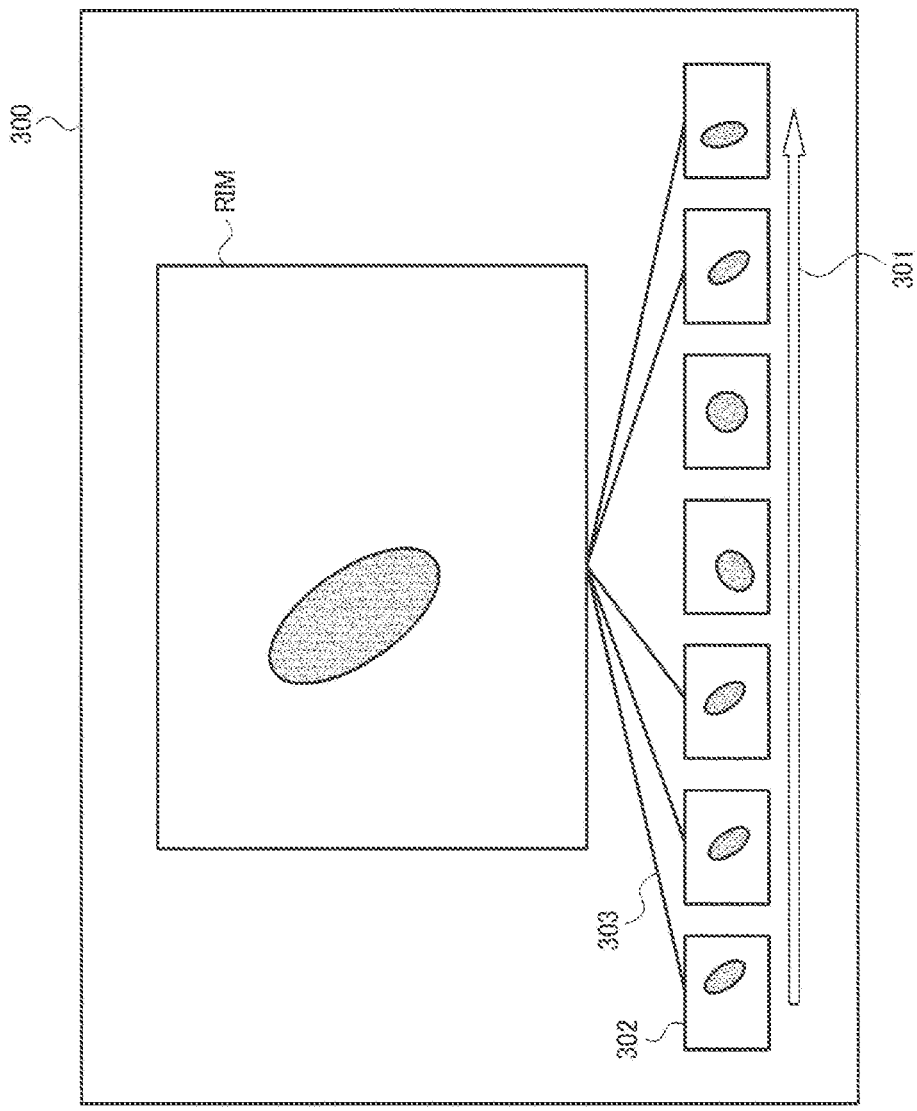
FIG. 7 illustrates an example of an image displayed on a display section in a second modification of the first configuration example.

In a second modification, display of an association state is performed. FIG. 7 illustrates an example of an image displayed on the display section 300 in the second modification.

The image output section 130 outputs, to the display section 300, association information 303 between the application target image RIM and each of medical images 302 other than the application target image RIM out of the plurality of medical images. Reference numeral 301 in FIG. 7 denotes an arrow indicating the passage of time. That is, the medical images 302 are displayed in time series along the arrow 301. The association information 303 is represented by a line connecting the application target image RIM and the medical image 302. The images connected with each line are those that have been determined to be imaging targets with a high degree of similarity and be associated. The images not connected with the line are those that have been determined to be the imaging targets with a low degree of similarity and not be associated.

This enables the user to determine the state of association between the application target image RIM and each medical image. For example, the user can determine whether an appropriate medical image is selected as the application target image RIM.

The input accepting section 140 accepts input to specify, as new application target images, any of the medical images 302 other than the application target image RIM. The input accepting section 140 changes the application target image based on the input accepted. That is, the user views the association information 303 displayed on the display section 300 and selects the relevant medical images when he or she determines that there exists an application target image that is more appropriate than the current application target image RIM. The input accepting section 140 determines the medical image selected by the user as the new application target image.

With this processing, the user can newly select, as an application target image, another medical image that he or she has determined to be appropriate as a medical image to which representative training information is to be applied, to apply the representative training information to the application target image. This enables the generation of training images that can achieve higher accuracy in machine learning.

Note that, after the user selected a new application target image, the image associating section 120 may reconfigure an associated image group, and then the image output section 130 may display the relevant association information on the display section 300. More specifically, the image associating section 120 may set, to a new associated image group, the medical images that are highly similar to the application target image newly selected by the user to output the relevant association information to the image output section 130.

In a third modification, adjustment for display of specific regions is performed. FIG. 8 illustrates a configuration example of the training data generating system 10 in the third modification. The processing section 100 further includes the detecting section 160 in FIG. 8. The image output section 130 includes a display adjuster 131. Note that the description of components already discussed will be omitted as appropriate.

Figure 9:
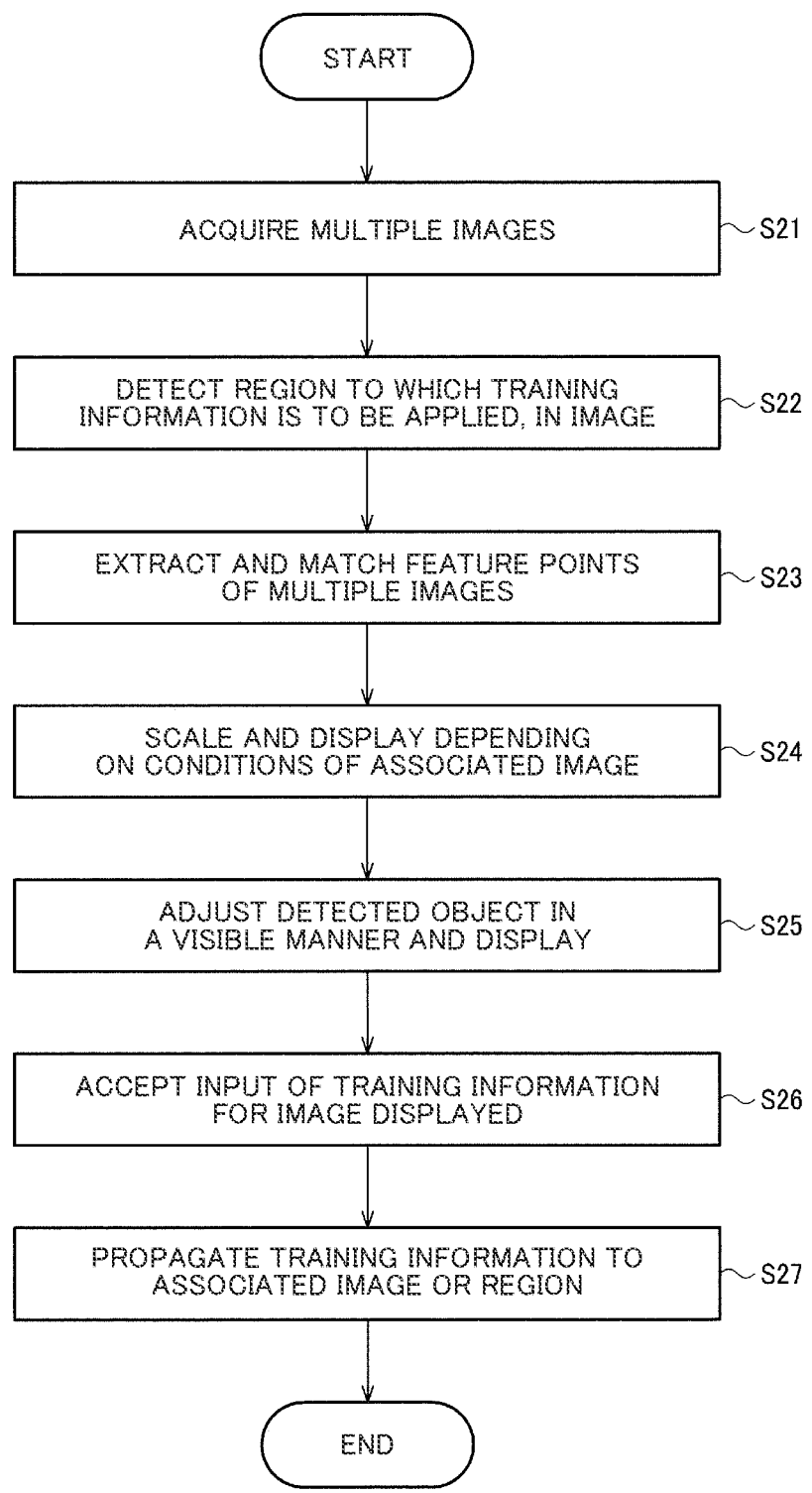
FIG. 9 is a flowchart illustrating a flow of process in the third modification of the first configuration example.

FIG. 9 is a flowchart illustrating a flow of process in the third modification. A description of steps S21, S26, and S27, which are similar to steps S1, S4, and S5 in FIG. 2, respectively, is omitted here.

In step S22, the detecting section 160 detects a specific region in each medical image out of the plurality of medical images. The specific region is an area to which training information is to be applied. In step S23, the image associating section 120 extracts feature points from each medical image out of the plurality of medical images to perform matching between the images for the feature points. At this time, the image associating section 120 may extract feature points based on the specific region detected by the detecting section 160. The image associating section 120, for example, may extract feature points that characterize a specific region.

In step S24, the display adjuster 131 scales an application target image depending on conditions of the associated image to display it on the display section 300. In the associated image group, for example, the display adjuster 131 scales the application target image such that a specific region has the appropriate size when the size of the specific region seen in the image is large or small. In step S25, the display adjuster 131 adjusts such that the detected specific region is easily viewable to display the application target image on the display section 300. The display adjuster 131 performs such as parallel translation of the specific region such that it is located in the center of a screen and a rotation process and projective transformation such that the specific region is easily viewable. The projective transformation represents a transformation that changes a tilt of the plane having a specific region, or equivalently, that changes an angle formed by the plane having the specific region and a camera line-of-sight. Note that either or both of steps S25 and S24 may be implemented.

In accordance with the present embodiment, the display adjuster 131 applies geometric transformation to the application target image before outputting it to the display section 300. The geometric transformation includes such as parallel translation, a rotation, scaling, a projective transformation, or combinations thereof.

With this processing, the geometric transformation can be performed such that the specific region to which the representative training information is applied by the user is easily viewable. This enables the specific region to be presented to the user in an easily viewable manner, and reduction of the user's workload, or the user to accurately apply the representative training information.

In accordance with the present embodiment, the detecting section 160 detects information for a specific region from the plurality of medical images through image processing. The display adjuster 131 performs the geometric transformation based on the information for the detected specific region to adjust display of the specific region. The image processing is an image recognition process that recognizes the position, the area, or the like of the specific region from the image. Various techniques can be used for the image recognition process. One example thereof includes a machine learning-based image recognition technique or a feature amount extraction-based image recognition technique. The detected information for the specific region contains a position, size, contour, or area of the specific region, or combinations thereof. The use of the information as above enables such as the parallel translation, rotation, or scaling to be performed such that the specific region is properly displayed.

With this processing, the detecting section 160 detects in advance the specific region to which the training information is to be applied and consequently, the display adjuster 131 can geometrically transform the application target image such that the above specific region is properly displayed.

Figure 10:
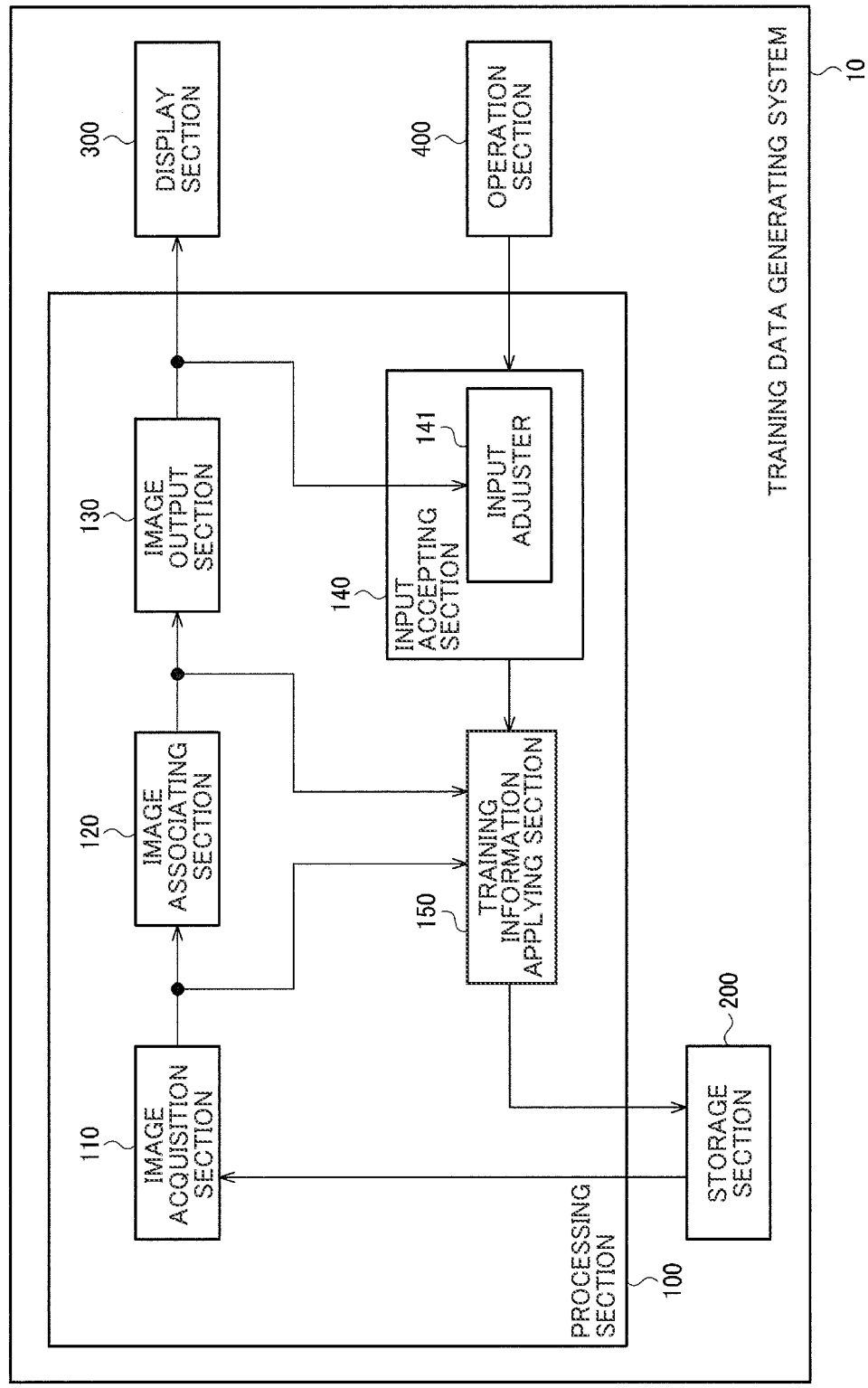
FIG. 10 illustrates a configuration example of the training data generating system in a fourth modification of the first configuration example.

In a fourth modification, adjustment for the input representative training information is performed. FIG. 10 illustrates a configuration example of the training data generating system 10 in the fourth modification. The input accepting section 140 includes an input adjuster 141 in FIG. 10. Note that the description of components already discussed will be omitted as appropriate.

FIG. 11 illustrates a first operation example of the input adjuster 141. The input adjuster 141 detects estimated contour information ATES for a specific region in the application target image through the image processing. The input accepting section 140 accepts representative contour information ATINb indicative of a contour of a specific region in the application target image as the representative training information. The input adjuster 141 corrects the representative contour information ATINb based on the estimated contour information ATES when the estimated contour information ATES has equal to or more than a predetermined degree of reliability.

The input adjuster 141 performs the image recognition process by AI processing to output the estimated contour information ATES and the degree of reliability of the estimation. For example, the degree of reliability for each position along a contour is output. The input adjuster 141 corrects the representative contour information ATINb based on the estimated contour information ATES for areas where the reliability is equal to or more than the predetermined degree. The input adjuster 141, for example, replaces the representative contour information ATINb with the estimated contour information ATES for areas where the reliability is equal to or more than the predetermined degree. The input adjuster 141 outputs, to the training information applying section 150, the corrected representative contour information as the final representative training information ATF.

In accordance with the present embodiment, when estimated contour information made based on the image processing is reliable, the representative contour information input by the user is corrected based on the estimated contour information. For example, the cases are considered in which contour information input by the user is inaccurate, however, even in the presence of such a case, the contour information can be corrected to be accurate. Then, the correction is performed only when the estimated contour information is reliable, thus enabling the highly accurate correction.

Figure 12:
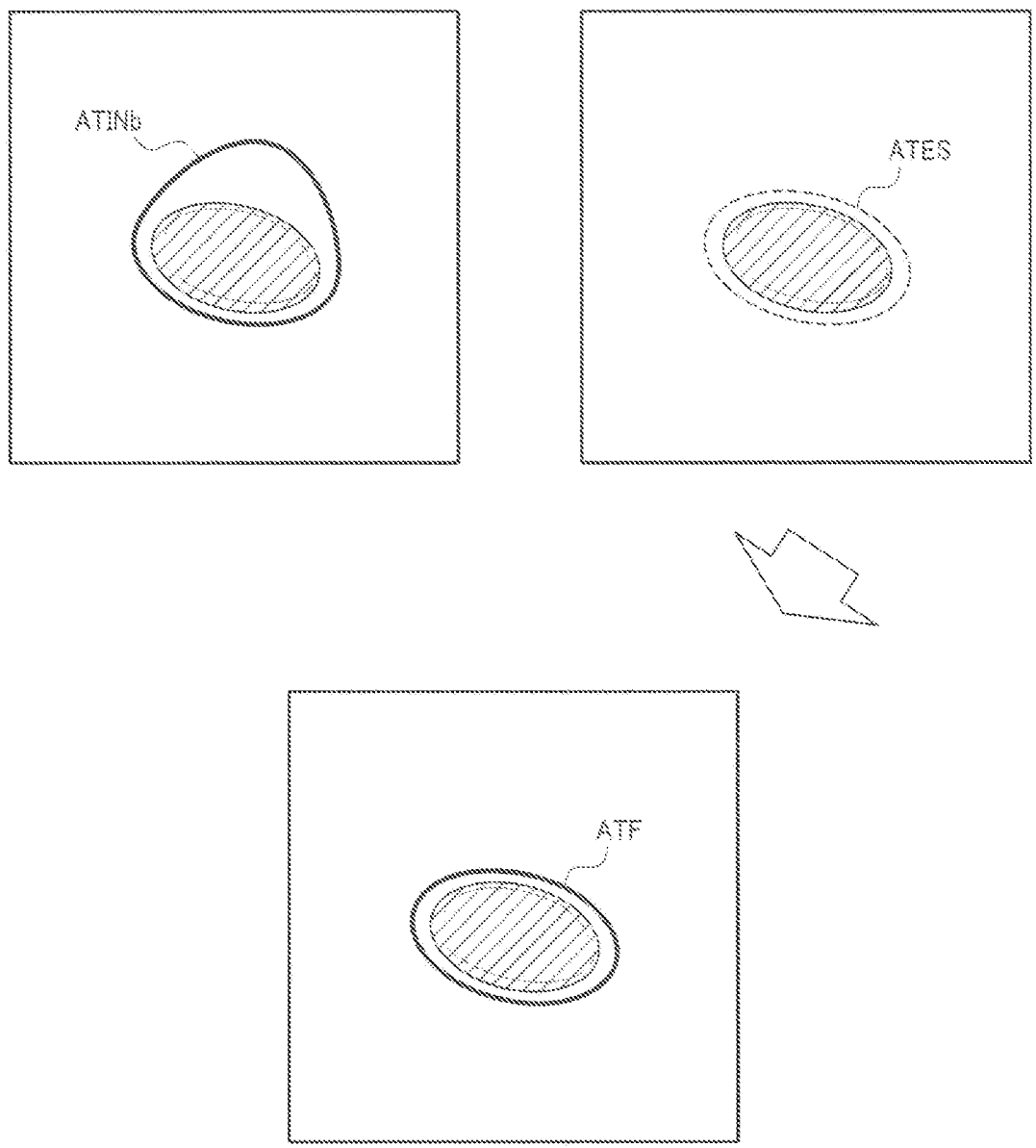
FIG. 12 illustrates a second operation example of the input adjuster.

FIG. 12 illustrates a second operation example of the input adjuster 141. The input adjuster 141 detects the estimated contour information ATES for a specific region in the application target image through the image processing. The input accepting section 140 accepts the representative contour information ATINb indicative of a contour of a specific region in the application target image as the representative training information. The input adjuster 141 outputs the representative training information based on the estimated contour information ATES when the estimated contour information ATES has equal to or more than a predetermined degree of reliability, and outputs the representative training information based on the representative contour information ATINb when the estimated contour information ATES has less than the predetermined degree of reliability.

The input adjuster 141 performs the image recognition process by the AI processing to output the estimated contour information ATES and the degree of reliability of the estimation. For example, the degree of reliability for the entire contour is output. The input adjuster 141 outputs, to the training information applying section 150, the estimated contour information ATES as the final representative training information ATF in the presence of equal to or more than the predetermined degree of reliability. Additionally, the input adjuster 141 outputs, to the training information applying section 150, the representative contour information ATINb as the final representative training information ATF in the presence of less than the predetermined degree of reliability. FIG. 12 illustrates the case where the estimated contour information ATES is selected.

In a fifth modification, the feature point is extracted again based on the input representative training information. A hardware configuration of the training data generating system 10 is the same as those in FIG. 1.

The image associating section 120 extracts a feature point indicative of a feature of an image from each medical image in the plurality of medical images to perform the association of medical images each including the feature point in common with each other out of the plurality of medical images, and thereby generates an associated image group. The input accepting section 140 accepts representative contour information indicative of a contour of a specific region in an application target image as representative training information. The image associating section 120 extracts the feature point to perform the association again based on a position of the contour of the representative contour information when the contour of the representative contour information is away from the feature point by equal to or more than a predetermined distance.

Specifically, the image associating section 120 calculates distance between contour of the representative contour information and a feature point of the application target image. The distance represents, for example, the distance between the closest point of the contour to a feature point and the feature point. When the application target image has a plurality of feature points, the distance is determined for each feature point, of which such as the shortest or average distance is determined as the final distance. The image associating section 120 extracts the feature points in each medical image again when the obtained distance is equal to or more than a predetermined distance. Then, the image associating section 120 extracts the feature point present near the contour of the representative contour information input by the user to reconfigure the associated image group with the feature point.

In accordance with the present embodiment, the feature point is extracted again based on the contour of the representative contour information input by the user, thus allowing the feature point relevant to the specific region recognized by the user to be extracted again. The reconfiguration of the associated image group with the feature point yields the associated image group which is associated properly by the feature point of the specific region. This enables the training information applying section 150 to accurately apply the contour information to each medical image based on the representative contour information.

3. Second Configuration Example

Figure 13:
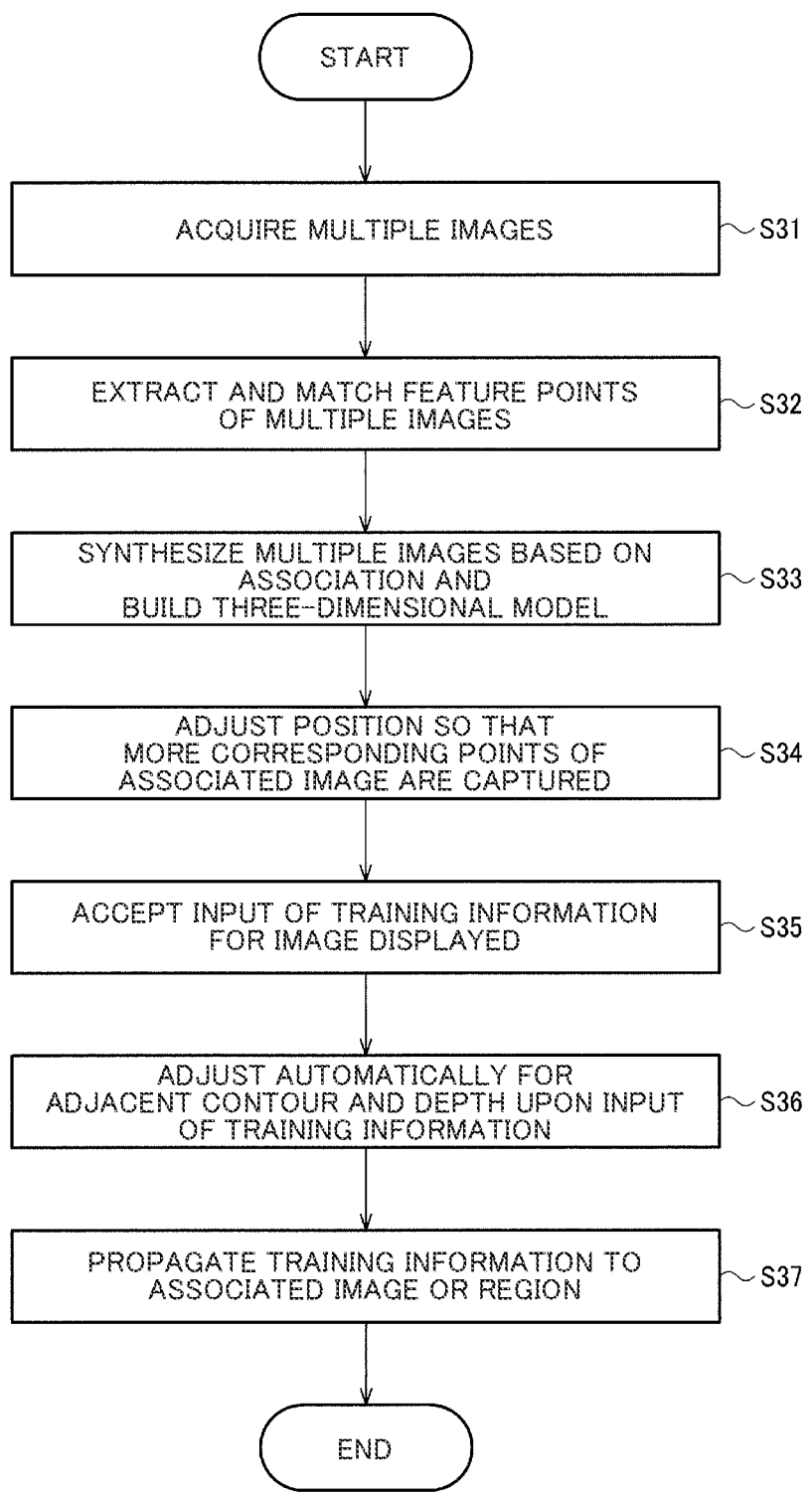
FIG. 13 is a flowchart illustrating a flow of process in a second configuration example.

A second configuration example of the training data generating system 10 is now described. A hardware configuration of the training data generating system 10 is the same as those in FIG. 1. FIG. 13 is a flowchart illustrating a flow of process in the second configuration example. A description of steps S31 and S32, which are similar to steps S1 and S2 in FIG. 2, respectively, is omitted here.

In step S33, the image associating section 120 synthesizes a plurality of medical images based on the results of association in step S32 to build a three-dimensional model. In step S34, the image output section 130 adjusts a position of the three-dimensional model such that more corresponding points in the associated medical images are captured, to output a two-dimensional image of the position as an application target image to the display section 300. In step S35, the input accepting section 140 accepts input of representative training information for the application target image. Examples of the training information are considered to include, but are not limited to, a bounding box, a contour, and a region.

In step S36, the input accepting section 140 automatically adjusts the input representative training information so as to match the adjacent contour in the three-dimensional model, or automatically adjusts the input representative training information depending on the depth of the three-dimensional model. In step S37, the training information applying section 150 applies the training information to the medical image or region associated with the three-dimensional model based on the applied representative training information to the three-dimensional model.

Figure 14:
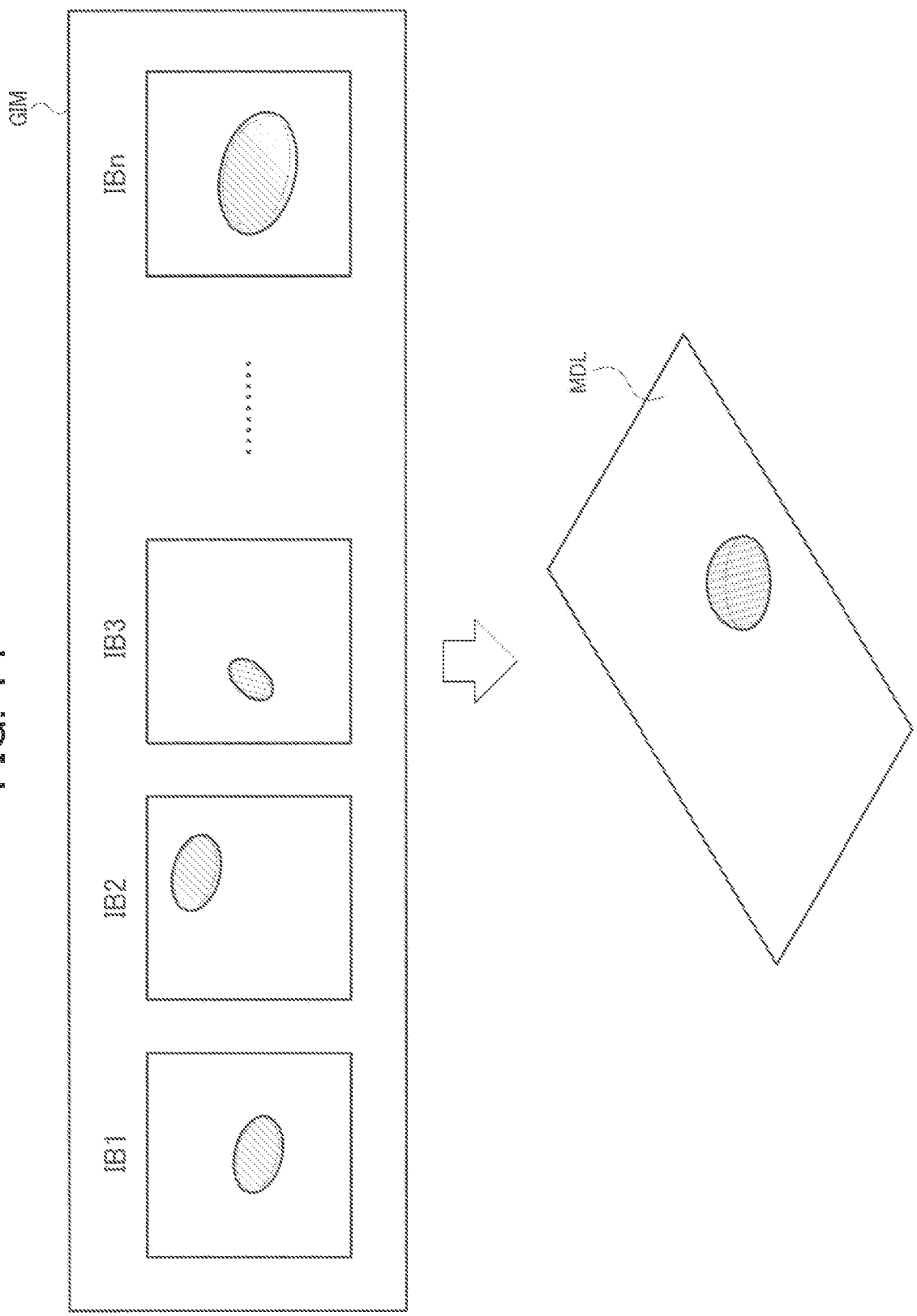
FIG. 14 illustrates an operation of an image associating section.

FIG. 14 illustrates an operation of the image associating section 120. The feature points are extracted from the medical images IB1 to IBn as in FIG. 3, which is not illustrated in FIG. 14, and the medical images with high similarities of the imaging target are associated with each other as the associated image group GIM.

The image associating section 120 uses association of the medical images IB1 to IBn included in the associated image group GIM to synthesize a three-dimensional model MDL based on the medical images IB1 to IBn. Specifically, the image associating section 120 estimates at what camera position and line-of-sight direction each medical image has been captured based on the feature points in each medical image and association of the feature points between the medical images with each other to estimate the three-dimensional model MDL based on the estimation result. Methods for synthesizing the three-dimensional model MDL can employ the Structure from Motion (SfM), for example.

Figure 15:
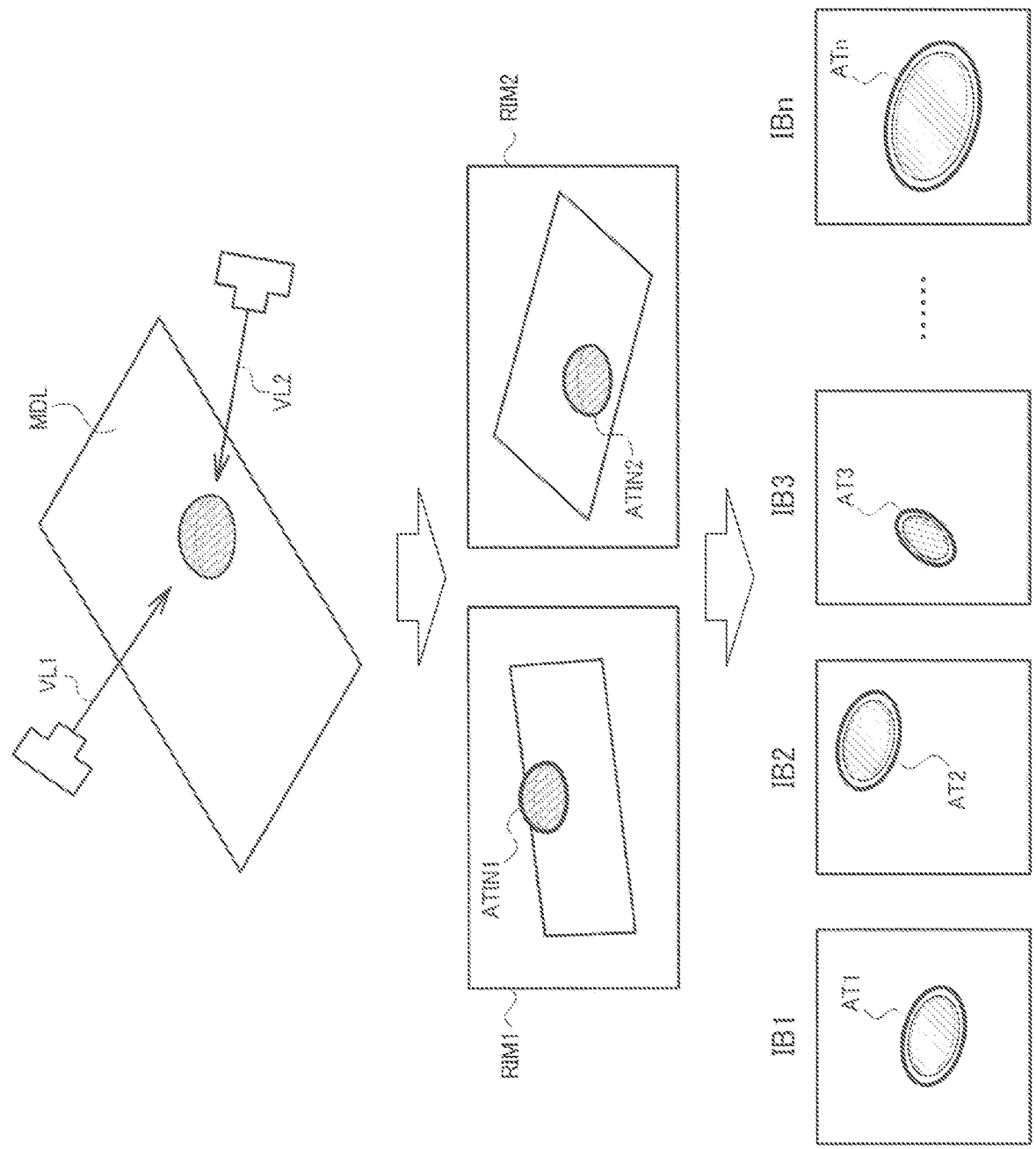
FIG. 15 illustrates operations of an image output section, an input accepting section, and a training information applying section.

FIG. 15 illustrates operations of the image output section 130, the input accepting section 140, and the training information applying section 150. The image output section 130 generates application target images RIM1 and RIM2 based on the three-dimensional model MDL. The application target images RIM1 and RIM2 each represent the two-dimensional image when the three-dimensional model MDL is viewed from visual lines VL1 and VL2, respectively. For example, the visual line VL2 is viewed in the opposite direction to the visual line VL1. That is, given that the appearance of the three-dimensional model MDL in the application target image RIM1 is the front, the appearance of the three-dimensional model MDL in the application target image RIM2 is therefore the back.

The user applies the representative training information ATIN1 and ATIN2 to the application target images RIM1 and RIM2, respectively. FIG. 15 illustrates a case where training information represents contour information. The input accepting section 140 applies the representative training information to the three-dimensional model MDL based on the representative training information ATIN1 and ATIN2. That is, the input accepting section 140 generates a contour of a specific region in the three-dimensional model MDL based on the contour of the representative training information ATIN1 and ATIN2. For example, when the specific region is a convex portion, the boundary defined by the convex portion and the surface other than that of the convex portion is the contour of the specific region in the three-dimensional model MDL.

The training information applying section 150 applies the training information AT1 to ATn to the medical images IB1 to IBn in the associated image group GIM based on the applied representative training information to the three-dimensional model MDL. Upon generation of the three-dimensional model MDL, a camera position and a line-of-sight direction responsive to each medical image are estimated. In addition, as long as a three-dimensional model is generated, the distance between each point of the model and the camera position is also estimated. The training information applying section 150 uses the camera position and the line-of-sight direction to convert the representative training information for the three-dimensional model MDL into the training information AT1 to ATn for the medical images IB1 to IBn.

In accordance with the present embodiment, the image output section 130 outputs, to the display section 300, an image generated with the associated image group GIM as an application target image.

Since the associated image group GIM is associated based on similarities of an imaging target, the image generated with such associated image group GIM becomes the image relevant to the imaging target. Displaying such image as the application target image to the display section 300 properly presents the imaging target to the user.

Additionally, in the present embodiment, the image output section 130 generates the three-dimensional model MDL of the imaging target based on the associated image group GIM to output, to the display section 300, the images RIM1 and RIM2 made based on the three-dimensional model MDL as the application target image.

This enables the three-dimensional model MDL of the imaging target to be presented to the user. The use of the three-dimensional model MDL allows for proper application of training information to lesions and other area where a three-dimensional structure is considered important. Furthermore, it is possible, irrespective of how an imaging target appears in each medical image, to present the user with a three-dimensional model MDL viewed from any camera line-of-sight and display an application target image suitable for applying representative training information.

Specifically, the image output section 130 displays an application target image when viewing the three-dimensional model MDL at camera line-of-sight where more corresponding points are captured. The corresponding points represent feature points in common with between medical images that are used to build the three-dimensional model MDL. Since association of the feature points is used to build the three-dimensional model MDL, positions of the feature points in the three-dimensional model MDL are known. It is thus possible to know at what camera line-of-sight when viewing the three-dimensional model MDL more corresponding points are captured, so that the application target image viewed at such camera line-of-sight is displayed. FIG. 15 illustrates two of the application target images RIM1 and RIM2. For example, the image viewed at the camera line-of-sight with the largest number of corresponding points is selected as any one of the images RIM1 and RIM2.

The fact that an image with more corresponding points being captured is displayed indicates that an area with highly accurate association is displayed when building the three-dimensional model MDL based on the associated image group GIM. Such application target image is considered to have a highly accurate association with each medical image in the associated image group GIM. This ensures that highly accurate training information can be generated when the training information is applied to each medical image based on the representative training information applied to the application target image.

Additionally, in the present embodiment, the image output section 130 outputs, to the display section 300, the plurality of two-dimensional images RIM1 and RIM2 with different line-of-sight directions with respect to the three-dimensional model MDL as the plurality of application target images. The input accepting section 140 accepts the representative contour information indicative of a contour of a specific region in the application target image as representative training information ATIN1 and ATIN2 for each of the plurality of the two-dimensional images. The training information applying section 150 applies contour information to the medical images IB1 to IBn included in the associated image group GIM as the training information AT1 to ATn.

When the three-dimensional model MDL is viewed at a single line-of-sight direction, areas may be present that are invisible behind such as a convex portion. In accordance with the present embodiment, displaying the plurality of two-dimensional images with the different line-of-sight directions displays the two-dimensional images in which the three-dimensional model MDL is viewed from various directions and applies the representative contour information to each of the two-dimensional images. As a result, contour information is applied to the three-dimensional model MDL without missing. Note that the number of two-dimensional images displayed is not limited to two, and may be multiple while two of the two-dimensional images are displayed as the application target image in FIG. 15.

In the above, the description has been given using an example of a case where the "image generated with an associated image group" is an image based on the three-dimensional model MDL, but not limited thereto, a developed view, illustrating such as digestive tract, generated based on the associated image group GIM may be applicable as in the modifications described below.

4. Modifications of the Second Configuration Example

In a first modification, adjustment of input of representative contour information is performed. A hardware configuration of the training data generating system 10 is the same as those in FIG. 10.

The input accepting section 140 accepts the representative contour information indicative of a contour of a specific region in the application target images RIM1 and RIM2 as the representative training information ATIN1 and ATIN2. The input adjuster 141 adjusts the representative contour information input based on the contour and depth of the three-dimensional model MDL.

The depth represents the depth of the three-dimensional model MDL when viewed as the two-dimensional image displayed as the application target image and corresponds to camera line-of-sight when generating the two-dimensional image. For example, in a case where a convex portion of the three-dimensional model MDL is contoured, when the contour applied by the user is viewed in a depth direction, a plurality of surfaces of the three-dimensional model MDL may be present in such depth direction. In such cases, the input adjuster 141 adjusts the representative contour information such that the closest surface is contoured. The input adjuster 141 also adjusts the representative contour information so as to match the contour of the three-dimensional model MDL adjacent to the representative contour information when the representative contour information applied by the user is apart from a contour of the three-dimensional model MDL in the application target image.

In accordance with the present embodiment, the representative contour information in the three-dimensional model MDL can be applied properly based on the representative contour information applied to the application target image, which is a two-dimensional image. That is, the depth of the three-dimensional model MDL is considered, and thereby the representative contour information is applied to the contour intended by the user. Furthermore, consideration of the contour of the three-dimensional model MDL allows correction to accurate contour information even in the case where, for example, the contour information input by the user is inaccurate.

Figure 16:
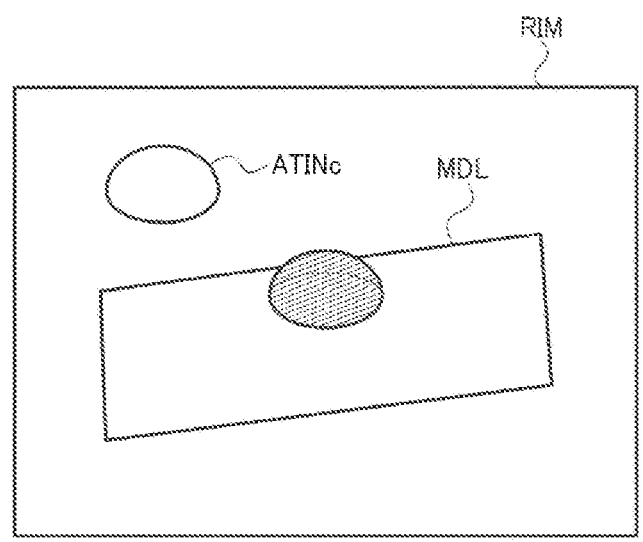
FIG. 16 illustrates a second modification of the second configuration example.

In a second modification, detection of an input error of representative contour information is performed. A hardware configuration of the training data generating system 10 is the same as those in FIG. 1. FIG. 16 illustrates the second modification. FIG. 16 illustrates one application target image, but a plurality of application target images may be displayed as described above.

The image output section 130 generates a two-dimensional image based on the three-dimensional model MDL to output the two-dimensional image as the application target image RIM. The input accepting section 140 accepts representative contour information ATINc indicative of a contour of a specific region in the application target image RIM as representative training information. In a case where the three-dimensional model MDL is absent on the depth of the contour of the representative contour information ATINc in a line-of-sight direction when the two-dimensional image is generated based on the three-dimensional model MDL, the input accepting section 140 outputs error information instructing a change of the line-of-sight direction.

FIG. 16 shows that the three-dimensional model MDL displayed in the application target image RIM and the representative contour information ATINc do not overlap. That is, the three-dimensional model MDL is absent on the depth of the contour of the representative contour information ATINc in the line-of-sight direction. For this case, the input accepting section 140 outputs the error information. For example, the image output section 130 receives input of error information and causes the display section 300 to display indication prompting the user to change the line-of-sight direction based on the error information. Alternatively, the image associating section 120 receives input of error information and performs again association of medical images to generate again an associated image group and a three-dimensional model based on the error information. And then, the image output section 130 displays the application target image again.

In accordance with the present embodiment, upon reception of input of the representative contour information ATINc inappropriate for the three-dimensional model MDL, the error information is output to prevent such inappropriate representative contour information from being used. For example, the cases are considered in which an appropriate three-dimensional model is not generated, and camera line-of-sight is inappropriate when presenting the three-dimensional model to the user. In accordance with the present embodiment, even in the presence of such cases, the inappropriate representative contour information can be prevented from being used.

Figure 17:
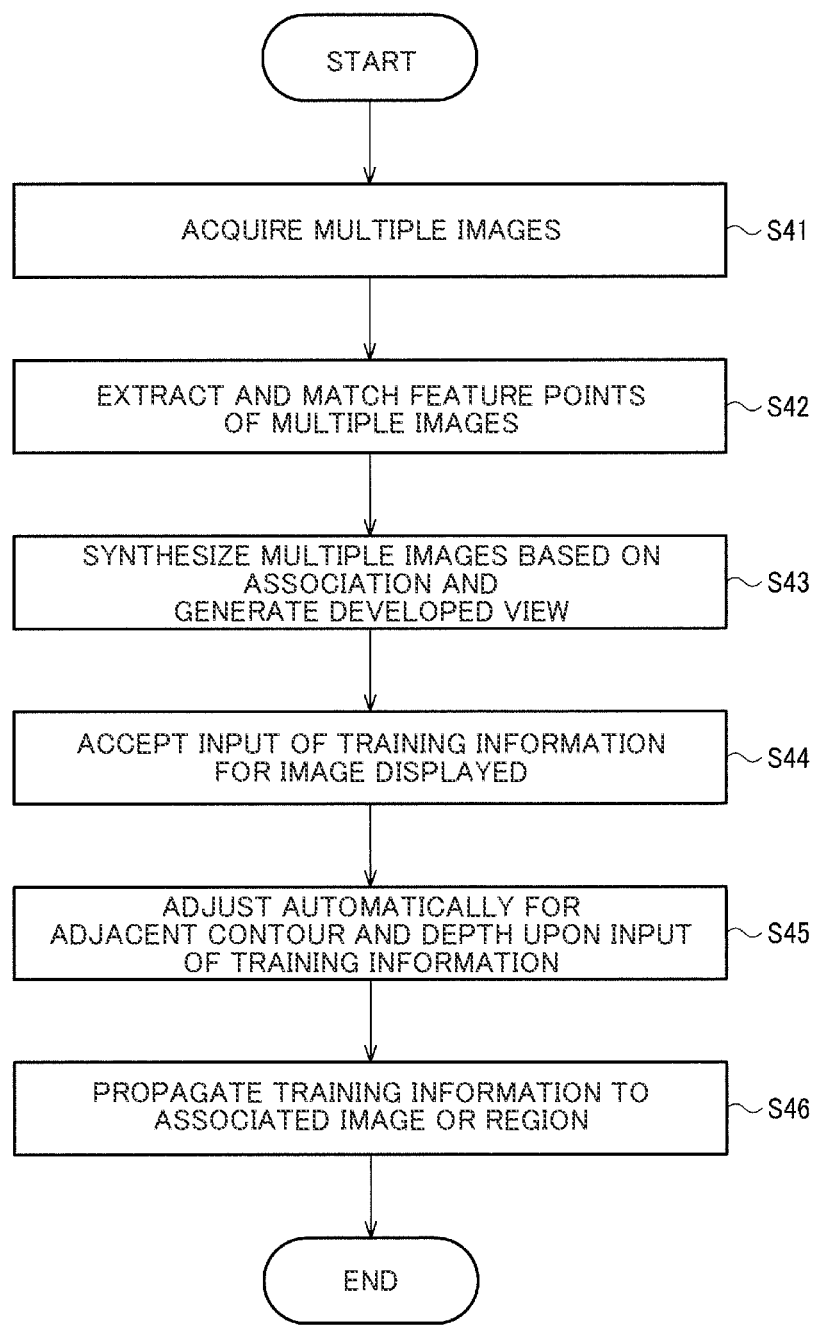
FIG. 17 is a flowchart illustrating a flow of process in a third modification of the second configuration example.
Figure 18:
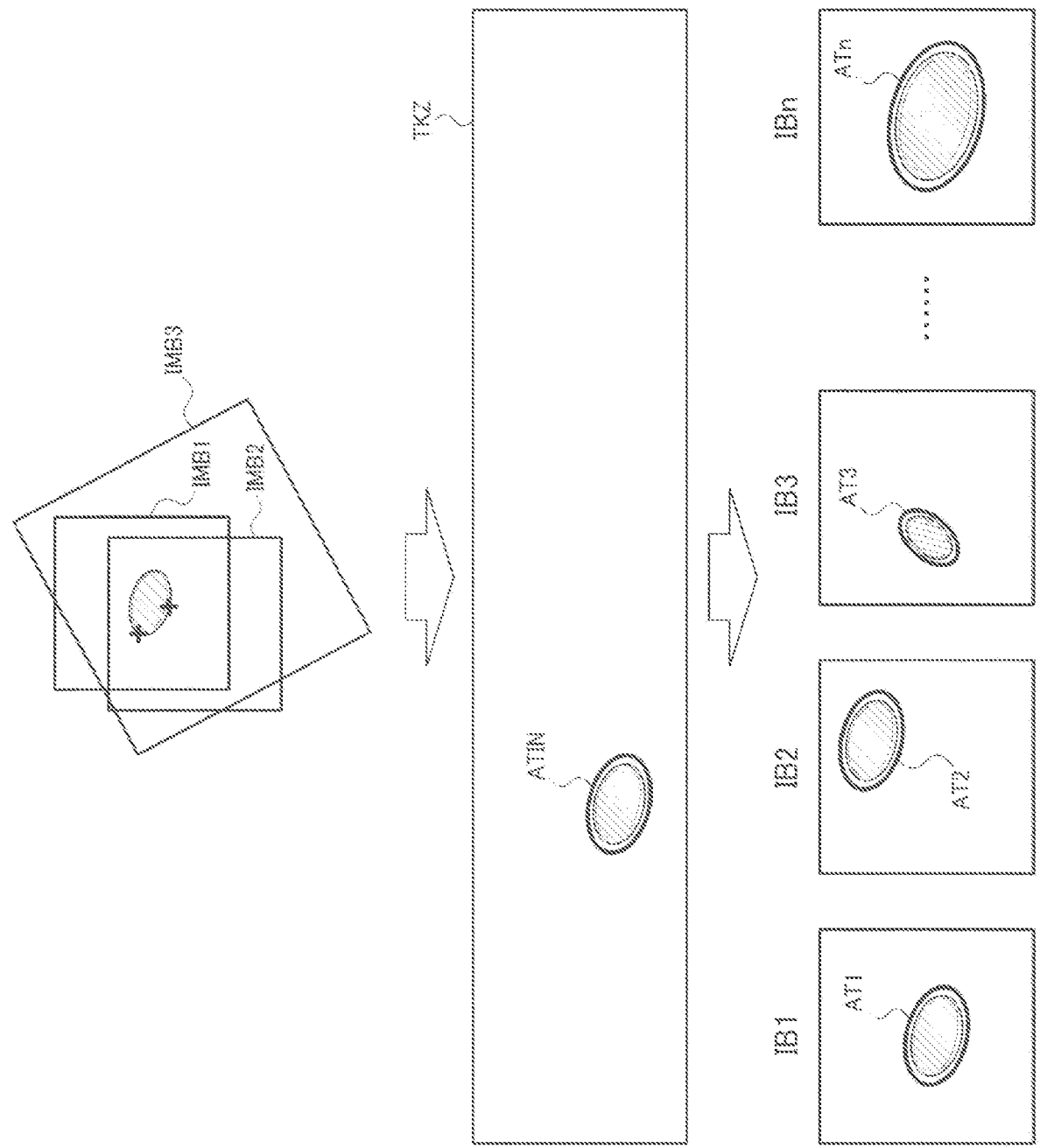
FIG. 18 illustrates the third modification of the second configuration example.

In a third modification, generation of a developed view based on an associated image group and display of an application target image based on the developed view are performed. In other words, in the third modification, the "image generated with an associated image group" is a developed view. FIG. 17 is a flowchart illustrating a flow of process in the third modification. A description of steps S41 and S42, which are similar to steps S1 and S2 in FIG. 2, respectively, is omitted here. FIG. 18 illustrates the third modification.

In step S43, the image associating section 120 synthesizes the medical images IB1 to IBn based on association of the medical images IB1 to IBn in the associated image group GIM to generate a developed view TKZ. Specifically, the image associating section 120 stacks the medical images IB1 to IBn based on correspondence of feature points between medical images with each other such that positions of the corresponding feature points are consistent with each other, and thereby generates the developed view TKZ. FIG. 18 illustrates the state of stacking the images IB1 to IB3 among IB1 to IBn. The images IB4 to IBn are also to be stacked.

The image output section 130 outputs, to the display section 300, an application target image based on the developed view TKZ. The image output section 130, for example, may display the entire developed view TKZ on the display section 300, or alternatively, may display a part of the developed view TKZ in which a specific region is captured, on the display section 300.

In step S44, the input accepting section 140 accepts the representative training information ATIN input by the user. FIG. 18 illustrates a case where training information represents contour information. The input accepting section 140 automatically adjusts the input representative training information so as to match the adjacent contour in the developed view.

In step S46, the training information applying section 150 applies the training information to the medical image or region associated with the developed view based on the representative training information applied to the developed view. In step S43, since the medical images IB1 to IBn are stacked to generate the developed view TKZ, positions of each medical image in the developed view TKZ are known. The training information applying section 150 uses the positions of each medical image in the developed view TKZ to convert the representative training information ATIN into the training information for each medical image.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. A training data generating system comprising:
a processor comprising hardware, the processor being configured to:
acquire a plurality of medical images;
associate medical images with each other which are included in the plurality of medical images based on similarities of an imaging target to generate an associated image group comprising medical images associated with each other;
accept input of representative contour information indicative of a contour of a specific region in an application target image in the associated image group as representative training information; and apply contour information, as training information, to each medical image included in the associated image group to generate a plurality of training images for a machine learning model, wherein the training information is based on the representative training information being applied to the application target image.

2. The training data generating system as defined in claim 1, wherein:
the processor is configured to output, to the display, a medical image selected from the associated image group as the application target image.

3. The training data generating system as defined in claim 2, wherein:
in a case where a number of medical images associated with each medical image in the association based on the similarity is considered as the number of associated images; and
the processor is configured to output, to the display, a medical image selected based on the number of associated images as the application target image.

4. The training data generating system as defined in claim 2, wherein:
the processor is configured to select the application target image from the plurality of medical images in the association based on a number of medical images associated with each medical image to determine a medical image associated with the application target image out of the plurality of medical images as the associated image group.

5. The training data generating system as defined in claim 2, wherein:
the processor is configured to apply geometric transformation to the application target image before outputting the application target image to the display.

6. The training data generating system as defined in claim 5, wherein the processor is configured to:
detect information of the specific region from the plurality of medical images through image processing; and
perform the geometric transformation based on the information of the specific region to adjust display of the specific region.

7. The training data generating system as defined in claim 2, wherein:
the processor is configured to detect estimated contour information of the specific region from the application target image through image processing and when the estimated contour information has equal to or more than a predetermined degree of reliability, corrects the representative contour information based on the estimated contour information.

8. The training data generating system as defined in claim 2, wherein:
the processor is configured to detect estimated contour information of the specific region from the application target image through image processing, outputs the representative training information based on the estimated contour information when the estimated contour information has equal to or more than a predetermined degree of reliability, and outputs the representative training information based on the representative contour information when the estimated contour information has less than the predetermined degree of reliability.

9. The training data generating system as defined in claim 1, wherein the processor is configured to:
extract a feature point indicative of a feature of an image from each medical image in the plurality of medical images to perform the association of medical images for generating the associated image group, each medical image among the plurality of medical images includes a common feature point in common with each other out of the plurality of medical images; and
use the common feature point to apply the contour information indicative of the contour of the specific region to the medical images included in the associated image group as the training information.

10. The training data generating system as defined in claim 1, wherein the processor is configured to:
extract a feature point indicative of a feature of an image from each medical image in the plurality of medical images to perform the association of medical images each including the feature point in common with each other out of the plurality of medical images, and thereby generates the associated image group; and
extract the feature point to perform the association again based on a position of the contour of the representative contour information when the contour of the representative contour information is away from the feature point by equal to or more than a predetermined distance.

11. The training data generating system as defined in claim 1, wherein:
the processor is configured to output, to the display, association information between the application target image and the medical images other than the application target image out of the plurality of medical images.

12. The training data generating system as defined in claim 11, wherein:
the processor is configured to accept input to specify any of the medical images other than the application target image out of the plurality of medical images as a new application target image to change the application target image based on the accepted input.

13. The training data generating system as defined in claim 1, wherein:
the processor is configured to output, to the display, the image generated by using the associated image group as the application target image.

14. The training data generating system as defined in claim 13, wherein;
the processor is configured to generate a three-dimensional model of the imaging target based on the associated image group to output, to the display, the image generated based on the three-dimensional model as the application target image.

15. The training data generating system as defined in claim 14, wherein the processor is configured to:
output, to the display, a plurality of two-dimensional images with different line-of-sight directions with respect to the three-dimensional model as a plurality of application target images;
accept input of the representative contour information for each of the plurality of two-dimensional images as the representative training information; and
apply the contour information to each medical image included in the associated image group as the training information.

16. The training data generating system as defined in claim 14, wherein:
the processor is configured to adjust the representative contour information input based on the contour and depth of the three-dimensional model.

17. The training data generating system as defined in claim 14, wherein the processor is configured to:

generate a two-dimensional image based on the three-dimensional model to output the two-dimensional image as the application target image; and in a case where the three-dimensional model is absent on a depth of the contour of the representative contour information in a line-of-sight direction when the two-dimensional image is generated based on the three-dimensional model, output error information instructing a change of the line-of-sight direction.

18. The training data generating system as defined in claim 1, wherein:
the processor is configured to output to a display, the application target image in the associated image group as the application target of representative training information.

19. A method of generating training data, the method comprising:
acquiring a plurality of medical images;
associating medical images with each other which are included in the plurality of medical images based on similarities of an imaging target to generate an associated image group comprising medical images associated with each other;
accepting input of representative contour information indicative of a contour of a specific region in an application target image in the associated image group as representative training information; and
applying contour information, as training information, to each medical image included in the associated image group to generate a plurality of training images for a machine learning model, wherein the training information is based on the representative training information being applied to the application target image.

20. A non-transitory computer readable recording medium storing thereon a computer program that causes a computer to perform a method comprising:
acquiring a plurality of medical images;
associating medical images with each other which are included in the plurality of medical images based on similarities of an imaging target to generate an associated image group comprising medical images associated with each other;
accepting input of representative contour information indicative of a contour of a specific region in an application target image in the associated image group as representative training information; and
applying contour information, as training information, to each medical image included in the associated image group to generate a plurality of training images for a machine learning model, wherein the training information is based on the representative training information being applied to the application target image.

* * * * *